US008691258B2

(12) United States Patent
Heruth et al.

(10) Patent No.: US 8,691,258 B2
(45) Date of Patent: Apr. 8, 2014

(54) ANTI-INFECTIVE MEDICAL DEVICE

(75) Inventors: Kenneth T. Heruth, Edina, MN (US); Christopher M. Hobot, Tonka Bay, MN (US); William J. Hooper, Lake Elmo, MN (US); Mark S. Lent, Brooklyn Park, MN (US); Ruchika Singhal, Minneapolis, MN (US); Robert M. Skime, Coon Rapids, MN (US); Randall V. Sparer, Andover, MN (US); Maura G. Donovan, St. Paul, MN (US); William J. Bertrand, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 1552 days.

(21) Appl. No.: 11/008,445

(22) Filed: Dec. 9, 2004

(65) Prior Publication Data

US 2006/0009806 A1 Jan. 12, 2006

Related U.S. Application Data

(60) Provisional application No. 60/529,461, filed on Dec. 12, 2003, provisional application No. 60/529,424, filed on Dec. 12, 2003.

(51) Int. Cl.
*A61F 13/00* (2006.01)
*A01N 25/00* (2006.01)

(52) U.S. Cl.
USPC .......................................... 424/422; 424/405

(58) Field of Classification Search
None
See application file for complete search history.

(56) References Cited

U.S. PATENT DOCUMENTS

| | | | | |
|---|---|---|---|---|
| 5,609,629 A | * | 3/1997 | Fearnot et al. | 623/1.42 |
| 5,622,657 A | * | 4/1997 | Takada et al. | 264/4.32 |
| 5,624,704 A | | 4/1997 | Darouiche et al. | |
| 5,869,079 A | * | 2/1999 | Wong et al. | 424/426 |
| 5,906,825 A | * | 5/1999 | Seabrook et al. | 424/404 |
| 6,846,939 B2 | * | 1/2005 | Nelson et al. | 552/205 |
| 7,259,210 B2 | * | 8/2007 | Puckett et al. | 525/193 |
| 2002/0173775 A1 | * | 11/2002 | Modak et al. | 606/1 |
| 2003/0118649 A1 | * | 6/2003 | Gao et al. | 424/471 |
| 2004/0215338 A1 | * | 10/2004 | Elkins et al. | 623/1.46 |
| 2005/0208094 A1 | * | 9/2005 | Armitage et al. | 424/423 |

FOREIGN PATENT DOCUMENTS

| | | | | |
|---|---|---|---|---|
| EP | 1174157 A1 | * | 1/2002 | A61L 29/00 |
| EP | 1362603 | | 11/2003 | |
| WO | WO 02/03890 | | 1/2002 | |
| WO | WO 03/030879 | * | 4/2003 | |

OTHER PUBLICATIONS

Price et al. Controlled release of antibiotics from coated othopedic implants. Journal of Biomedical Materials Research 1996 30:281-286.*
McDonnell et al. (Journal of Industrial Microbiology and Biotechnology 1998 21:184-186.*
Bain et al. European Journal of Pharmaceutical Sciences 1998 7:57-65.*
Tcholakian, "Durability of Anti-Infective Effect of Long-Term Silicone Sheath Catheters Impregnated with Antimicrobial Agents", Jul. 2001, p. 1990-1993, Antimicrobial Agents and Chemotherapy, American Society for Microbiology, Washington, DC, United States.

* cited by examiner

*Primary Examiner* — Juliet Switzer
*Assistant Examiner* — Caralynne Helm
(74) *Attorney, Agent, or Firm* — Mueting, Raasch & Gebhardt, P.A.

(57) ABSTRACT

Implantable medical devices (IMDS) having anti-infective properties are described. Anti-infective agents are disposed in, on, or about at least a portion of a surface of the medical device. The anti-infective agents are disposed in or on a vehicle, which may be in the form of a coating layer or covering. The vehicle may be biodegradable so that, over time, the anti-infective agent is removed from a tissue location into which the device is implanted, reducing the likelihood that microorganisms resistant to the anti-infective agent will develop. IMDs having an anti-infective agent and an anti-activity agent disposed therein, thereabout, or thereon are also described. The anti-activity agent interferes with the activity of the anti-infective agent, may be released from a surface at the IMD at a time when activity of the anti-infective agent is no longer desired, and may reduce the likelihood that microorganisms resistant to the anti-infective agent will develop.

11 Claims, 4 Drawing Sheets

ANTI-INFECTIVE MEDICAL DEVICE

RELATED APPLICATIONS

This application claims the benefit of priority to U.S. Provisional Patent Application Ser. Nos. 60/529,461 and 60/529,424, both filed on Dec. 12, 2003, which provisional applications are hereby incorporated herein by reference in their entireties.

FIELD

The present invention relates generally to implantable medical devices (IMDs).

BACKGROUND

At present, a wide variety of IMDs are commercially released or proposed for clinical implantation that include a housing that is implanted subcutaneously and typically include elongated medical electrical leads or drug delivery catheters that extend from the subcutaneous site to other subcutaneous sites or deeper into the body to organs or other implantation sites. Typically, the IMD includes a battery-powered implantable pulse generator (IPG) that is coupled with electrical medical leads, a battery-powered implantable monitor that may or may not be coupled with electrical medical leads, a battery-powered drug pump coupled with a drug delivery catheter, etc. Such IMDs include implantable cardiac pacemakers, cardioverter/defibrillators having pacing capabilities, other electrical stimulators including spinal cord, deep brain, nerve, and muscle stimulators, drug delivery systems, cardiac and other physiologic monitors, cochlear implants, etc. Typically, the battery-powered component of the IMD is implanted subcutaneously at a surgically prepared site, referred to as a "pocket". The surgical preparation and initial or replacement IMD implantations are conducted in a sterile field, and the IMD components are packaged in sterile containers or sterilized prior to introduction into the sterile field. However, despite these precautions, there always is a risk of introduction of microbes into the pocket. Surgeons therefore typically apply disinfectant or antiseptic agents to the skin at the surgical site prior to surgery (e.g., chlorhexidine, gluconate, povidone-iodine, isopropyl alcohol, ethyl alcohol), directly to the site before the incision is closed (e.g., gentamicin, vancomycin), and prescribe oral antibiotics for the patient to ingest during recovery (e.g., sefuroxin, gentamicin, rifamycin, vancomycin).

Despite these precautions, infections do occur. In addition, once the pocket becomes infected, the infection can migrate along the lead or catheter to the heart, brain, spinal canal or other location in which the lead or catheter is implanted. Such a migrating infection can become intractable and life-threatening, requiring removal of the IMD in the pocket and associated devices, such as leads and catheters. Removal of a chronically implanted lead or catheter can be difficult and dangerous. Aggressive systemic drug treatment is also provided to treat the infection.

There is long history of the actual or proposed use of anti-infective agents coated on IMDs for prevention of infection. For example, use of antibiotics and antiseptics has been described. However, actual use of antibiotics as coatings for permanently implantable medical devices has been limited. One reason logical reason for such limited use is the potential development of strains of bacterial resistant to the antibiotics. Over time, the effective concentration of the antibiotic in the coating will decrease to a level below which development of resistant bacterial strains becomes a concern.

SUMMARY

The present disclosure describes, inter alia, devices, systems, compositions, and methods useful for coating medical devices. The devices, systems, compositions, and methods may be used to reduce the risk of development of microbes resistant to anti-infective agents present in coatings, coverings, and the like of IMDs.

In an embodiment, the invention provides an implantable medical device having a surface onto, into, or about which surface an anti-infective agent in, on, or about a biodegradable or bioerodable vehicle is disposed. After implantation of the device in a tissue location, the vehicle degrades, removing the anti-infective agent source from the tissue location into which the device is implanted, and thus decreases the likelihood that resistant bacteria will develop in the tissue location into which the device is implanted. The anti-infective agent may be disposed in the vehicle such that the anti-infective agent is released upon erosion or degredation of the vehicle.

In an embodiment, the invention provides an IMD having a surface onto, into, or about which surface an anti-infective agent is disposed. An anti-activity agent, configured to decrease the activity of the anti-infective agent is also disposed in, on, or about the surface of the IMD. The anti-activity agent is released from the surface of the device at a time when the concentration of the anti-infective agent decreases to a level at which development of resistant microbes may be a concern. For example, the anti-activity agent may be released at a time when the anti-infective agent is present at the surface of the device at a subtherapeutic level, such as below the minimum inhibitory concentration (MIC) of the anti-infective agent. The MIC of the anti-infective agent may be determined against, e.g., *Stapholcoccus aureus*, *Staphlococcus epidermis*, *Pseudomonus auruginosa*, and *Candidia* Sp. The anti-infective agent and the anti-activity agent may be placed in, on, or about a vehicle disposed in, on, or about the surface of the device. The vehicle may be configured such that the anti-infective agent is released first and the anti-activity agent is released later in time.

Various embodiments of the invention provide one or more advantages over prior art methods, devices, and systems for preventing infection associated with implantation of a medical device. One advantage relates to the use of a bioerodable vehicle, which allows for close control of the duration with which an anti-infective agent is released. For example, once the vehicle has been essentially completely degraded or eroded, the antimicrobial agent will no longer be released and will no longer be present to allow for the generation of resistant microorganisms. The rate of degradation and erosion may also be controlled, thus the rate and duration of anti-micrbobial agent release may be controlled. Another advantage related to the bioerodable nature of the vehicle is that a microbe will not be able to permanently adhere to the vehicle. That is, the vehicle will degrade over time, thereby providing no surface for which a microbe may permanently adhere. This is in contrast to a non-degradable surface, such as the surface of a catheter. Further, the use of an anti-activity agent allows for an alternative or possible enhanced anti-infective therapy. An anti-activity agent, used with out without a biodegradable vehicle, serves to inactivate an anti-infective agent such that the likelihood that microbes will develop resistance to the anti-infective agent is reduced. These and other advantages will become evident to one of skill in the art upon reading the following detailed description in conjunction with the accompanying drawings.

Figure 1:
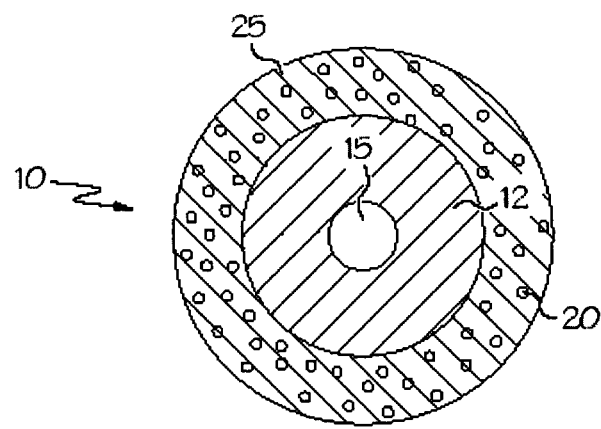
FIG. 1 is a diagrammatic illustration of a cross-section of a device comprising anti-infective agent disposed within a coating layer of the device.

The figures are not necessarily to scale.

DETAILED DESCRIPTION

In the following description specific embodiments are described. It is to be understood that other embodiments of the present invention are contemplated and may be made without departing from the scope or spirit of the present invention. The following detailed description, therefore, is not to be taken in a limiting sense.

All scientific and technical terms used in this application have meanings commonly used in the art unless otherwise specified. The definitions provided herein are to facilitate understanding of certain terms used frequently herein and are not meant to limit the scope of the present disclosure.

Implantable medical devices include drug pumps, neurostimulators, pacemakers, catheters, leads, extensions, shunts, and the like.

As used herein "therapeutic composition" refers to a composition that may exert a therapeutic effect, particularly an antimicrobial effect to prevent infection. A therapeutic composition according to various embodiments of the invention comprises a vehicle. The vehicle may be biodegradable, bioerodable, or biostable. The therapeutic composition may further include one or more anti-infective agents or one or more anti-activity agents. Examples of various components of such therapeutic compositions are discussed below.

Anti-Infective Agents

Any anti-infective agent may be used in accordance with various embodiments of the invention. As used herein "anti-infective agent" means an agent that treats or prevents an infection in a subject. An anti-infective agent may be any agent effective at killing or inhibiting the growth of a microorganism or a population of microorganisms. For example, the anti-infective agent may be an antibiotic or an antiseptic.

1. Antibiotic

Any antibiotic suitable for use in a human may be used in accordance with various embodiments of the invention. As used herein, "antibiotic" means an antibacterial agent. The antibacterial agent may have bateriostatic or bacteriocidal activities. Nonlimiting examples of classes of antibiotics that may be used include tetracyclines (e.g. minocycline), rifamycins (e.g. rifampin), macrolides (e.g. erythromycin), penicillins (e.g. nafcillin), cephalosporins (e.g. cefazolin), other beta-lactam antibiotics (e.g. imipenem, aztreonam), aminoglycosides (e.g. gentamicin), chloramphenicol, sufonamides (e.g. sulfamethoxazole), glycopeptides (e.g. vancomycin), quinolones (e.g. ciprofloxacin), fusidic acid, trimethoprim, metronidazole, clindamycin, mupirocin, polyenes (e.g. amphotericin B), azoles (e.g. fluconazole) and beta-lactam inhibitors (e.g. sulbactam). Nonlimiting examples of specific antibiotics that may be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al., U.S. Pat. No. 4,642,104, which is herein incorporated by reference in its entirety, may also be used. One of ordinary skill in the art will recognize other antibiotics that may be used.

It is desirable that the antibiotic(s) selected kill or inhibit the growth of one or more bacteria that are associated with infection following surgical implantation of a medical device. Such bacteria are recognized by those of ordinary skill in the art and include *Stapholcoccus aureus* and *Staphlococcus epidermis*. Preferably, the antibiotic(s) selected are effective against strains of bacteria that are resistant to one or more antibiotic.

To enhance the likelihood that bacteria will be killed or inhibited, it may be desirable to combine one or more antibiotic. It may also be desirable to combine one or more antibiotic with one or more antiseptic. It will be recognized by one of ordinary skill in the art that antimicrobial agents having different mechanisms of action or different spectrums of action may be most effective in achieving such an effect. In particular embodiments, a combination of rifanpin and micocycline is used.

2. Antiseptic

Any antiseptic suitable for use in a human may be used in accordance with various embodiments of the invention. As used herein, "antiseptic" means an agent capable of killing or inhibiting the growth of one or more of bacteria, fungi, or viruses. Antiseptic includes disinfectants. Nonlimiting examples of antiseptics include hexachlorophene, cationic bisiguanides (e.g. chlorhexidine, cyclohexidine), iodine and iodophores (e.g. povidone-iodine), para-chloro-meta-xylenol, triclosan, furan medical preparations (i.e. nitrofurantoin, nitrofurazone), methenamine, aldehydes (glutaraldehyde, formaldehyde), silver compounds (e.g., silver sulfadiazine) and alcohols. One of ordinary skill in the art will recognize other antiseptics.

It is desirable that the antiseptic(s) selected kill or inhibit the growth of one or more microbe that are associated with infection following surgical implantation of a medical device. Such bacteria are recognized by those of ordinary skill in the art and include *Stapholcoccus aureus, Staphlococcus epidermis, Pseudomonus auruginosa*, and *Candidia* Sp.

To enhance the likelihood that microbes will be killed or inhibited, it may be desirable to combine one or more antiseptics. It may also be desirable to combine one or more antiseptics with one or more antibiotics. It will be recognized by one of ordinary skill in the art that antimicrobial agents having different mechanisms of action or different spectrums of action may be most effective in achieving such an effect. In particular embodiments, a combination of chlorohexidine and silver sulfadiazine is used.

Anti-Activity Agent

Any anti-infective agent suitable for use in a human may be used in accordance with various embodiments of the invention. As used herein, "anti-activity agent" means an agent that interferes with the ability of an antibiotic or an antiseptic to exert its antibacterial or antiseptic effect. Anti-activity agents will be recognized by one of ordinary skill in the art. An anti-activity agent may exert its effect in a variety of ways. Generally, an anti-activity agent prevents binding of an antibiotic or antiseptic to the appropriate location of or in a microorganism. This can be accomplished by degrading or causing degradation of an antibiotic or antiseptic, binding to an antibiotic or antiseptic, binding to an appropriate location of or in the microorganism, etc. Preferably, an anti-activity agent interferes with the ability of an antibiotic or an antiseptic in such a way that decreases the likelihood that a microorganism will become resistant to the antibiotic or antiseptic. As concentrations of antimicrobial agents decrease, the likelihood that microorganisms will become resistant to the antimicrobial agent increases. Thus, it is preferred that an anti-activity agent exert its effect at a point in time when the concentration of antimicrobial agent is sub-therapeutic.

An anti-activity agent may be a pH-altering agent. A pH-altering agent may be an acid or a base. Acids and bases are generally well known and identifiable by those of ordinary skill in the art. Many antimicrobial agents are not stable in an acidic or a basic environment. Thus, presence of a pH-altering agent in the environment of an antimicrobial agent may cause the antimicrobial agent to degrade. In one embodiment, a pH-altering agent is citric acid.

Vehicle

The one or more anti-infective agent or anti-activity may be in or on a vehicle adapted to release the anti-infective agent or anti-activity. For example, the anti-infective agent or anti-activity may be embedded, coated, mixed, dissolved or dispersed on or in the vehicle. The vehicle may be disposed on, in or about at least a portion of an implantable medical device. For example, the vehicle may be in the form of a coating or covering. Alternatively, the vehicle may be delivered proximate to the implanted device as a therapeutic composition.

When the vehicle is attached to the device, ease of use and convenience are provided. When the vehicle is separate from the medical device, a surgeon has the option of not providing an antimicrobial agent along with the implanted device. In addition, not having the vehicle attached to the device prolongs the shelf life of the device. That is, anti-infective agents typically have shelf lives that are shorter than those of implantable medical devices. Thus attaching (or impregnating) an anti-infective agent to a medical device will shorten the effective shelf life of the device to that of the anti-infective agent.

A vehicle as described herein may take the form of a coating layer 25, 25' as described in association with the figures presented herewith.

1. Release Profile

The one or more anti-infective agents may be released from a vehicle at any rate sufficient to kill or inhibit growth of a microorganism. By "release" it is meant that the anti-infective agent is located at a position such that the anti-infective agent may contact a microorganism. In some circumstances, the anti-infective agent will be considered "released" while still in contact with the vehicle. Preferably an anti-infective agent is released for a duration sufficient to ward off a potential infection following implantation of a medical device. Generally, it should be sufficient for an anti-infective agent to be released for a duration sufficient to allow the surgical wound associated with implantation to heal, which can take about 30 days. In an embodiment, the duration of release of an anti-infective agent is between about 30 days and about 90 days. Release of an anti-infective agent for greater than 90 days may not be desirable, as resistance may develop. As resistance to antiseptics is generally minimal or non-existent, antiseptics may be released for longer durations than antibiotics in some embodiments of the invention.

In embodiments, where one or more anti-activity agent is included in or on the vehicle, it is preferred that the anti-activity agent is released at a time when effectiveness of the one or more anti-infective agent is sub-therapeutic. This may prevent development of resistant microorganisms. In some embodiments the anti-activity agent(s) is released about 30 days after implantation of the device, regardless of whether the anti-infective agent is at a subtherapeutic level. In various embodiments the anti-activity agent is released between about 30 days and about 90 days after implantation. In some embodiments, the anti activity agent(s) is released at about 90 days after implantation. It will be understood that some release of anti-activity agent may occur at a time earlier than about 30 days, about 30 days to about 90 days, or about 90 days, as the case may be, but that sustained sufficient amounts of the anti-activity agent will not be released until the appropriate time.

The rate at which anti-infective agent 20 or anti-activity agent may be released from a vehicle or coating layer 25, 25' into tissue may be controlled by properties of the vehicle or coating layers 25, as well as the manner in which anti-infective agent or anti-activity agent 200 is disposed on or in the vehicle or coating layers 25. A further discussion of such details is provided below.

2. Bioerodable Vehicle

Any bioerodable vehicle may be used, provided that it is suitable for use in humans. Preferably the vehicle possesses properties such that release rate of an anti-infective agent or anti-activity agent disposed in the vehicle has release profile characteristics similar to those discussed above. For example, the vehicle may substantially completely degrade with 90 days.

"Bioerodible" and "biodegradable" are used interchangeably herein.

The bioerodable vehicle may be a polymer, such as synthetic or natural bioabsorbable polymers. Any bioerodable polymer may be used. Such polymers are recognizable and identifiable by one or ordinary skill in the art. Non-limiting examples of synthetic, biodegradable polymers include: poly (amides) such as poly(amino acids) and poly(peptides); poly (esters) such as poly(lactic acid), poly(glycolic acid), poly (lactic-co-glycolic acid), and poly(caprolactone); poly (anhydrides); poly(orthoesters); poly(carbonates); and chemical derivatives thereof (substitutions, additions of chemical groups, for example, alkyl, alkylene, hydroxylations, oxidations, and other modifications routinely made by those skilled in the art), fibrin, fibrinogen, cellulose, starch, collagen, and hyaluronic acid, copolymers and mixtures thereof. The properties and release profiles of these and other suitable polymers are known or readily identifiable. It will be understood that the anti-infective agent 20 or anti-activity agent 200 may elute from an intact vehicle or may be released upon degradation of the vehicle.

In an embodiment the biodegradable vehicle is a microcapsule. In another embodiment, the bioerodable vehicle is in the form of a gauze or wrap.

3. Biostable Vehicles

In an embodiment of the invention, the vehicle is biostable. Any biostable vehicle may be used. Non-limiting examples of suitable biostable vehicles that may be used include organic polymers such as silicones, polyamines, polystyrene, polyurethane, acrylates, polysilanes, polysulfone, methoxysilanes, and the like. Other polymers that may be utilized include polyolefins, polyisobutylene and ethylene-alphaolefin copolymers; acrylic polymers and copolymers, ethylene-covinylacetate, polybutylmethacrylate; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; polycarbonates; polyoxymethylenes; polyimides; polyethers; epoxy resins; polyurethanes; rayon; rayon-triacetate; cellulose; cellulose acetate, cellulose butyrate; cellulose acetate butyrate; cellophane; cellulose nitrate; cellulose propionate; cellulose ethers; carboxymethyl cellulose; polyphenyleneoxide; and polytetrafluoroethylene (PTFE). In various embodiments of the invention, the biostable vehicle comprises silicone rubber or polyurethane.

When a biostable vehicle is used, an anti-activity agent is incorporated into or on the biostable vehicle. Generally when biostable vehicles, such as silicone or polyurethane, are used as vehicles, antimicrobials are released in an exponential manner. While, such vehicles may be suitable for use in short-term implantable devices, their release profile is generally not appropriate for long-term implantation, due to the sub-therapeutic concentrations of antimicorbial agent over time. Such sub-therapeutic concentration of antimicrobials may result in development of resistant microorganisms. To prevent microbial resistance, an anti-activity agent may be incorporated in or on a biostable vehicle and released at a point in time when anti-microbial agent concentration is sub-therapeutic.

4. Hydrogels

In an embodiment, the vehicle may be a hydrogel. Any hydrogel suitable for use in a human may be used. Hydrogels are known and recognizable by those of skill in the art. In an embodiment, the hydrogel may be a polyvinyl pyrrolidone (PVP) hydrogel.

A hydrogel may be permanently bound to a medical device. For example the hydrogel may be bound to the silicone catheter material. Generally, hydrophilic and smoothness qualities will last indefinitely when a PVP hydrogel is bound to a silicone catheter material, which may provide resistance to bacterial adhesion for an indefinite period.

Hydrogel coated devices may be pre-soaked in a solution comprising one or more antimicrobial agents. The antibiotic may be released for several days or longer. The release profile may vary depending on the antimicrobial agent.

For illustration, laboratory characterization was performed using Vancomycin pre-soaked onto a BioGlide® catheter. To determine the effective rate of release for pre-absorbed antibiotic, segments of grafted and control catheters were prepared by soaking in Vancomycin. The catheter segments were placed individually into $10^5$ CFU/mL broth cultures of *S. epidermidis*. The segments were retrieved from the first broth cultures after 24 hours and introduced into similar fresh cultures where they remained for an additional 24 hours. Finally the catheters were transferred to a third set of similar, fresh cultures and allowed to reside there for yet another 24 hours. Broth cultures that had hosted antibiotic soaked catheter segments were analyzed for percent transmission of light. A highly turbid appearing culture having a low percent light transmission value indicates the presence of a large number of bacterial cells. Inversely, broth cultures having a high percentage of light transmission are relatively clear in appearance indicating a low number of bacterial cells are present. Culture tubes were compared for the degree of bacterial growth between BioGlide® and control catheter segments and for the order in which the culture had hosted the antibiotic soaked catheter samples.

Luxuriant bacterial growth was apparent in all the culture tubes that had hosted the antibiotic pre-soaked control catheters. There was no apparent difference in the amount of growth between the tubes used for the first, second or third 24 periods. For the antibiotic pre-soaked BioGlide® catheters, no bacterial growth was detected in the culture tubes that had hosted these samples for the first or second 24-hour period. The culture tube from the third 24-hour period showed growth levels comparable to that found in the tubes that had hosted the control catheter segments.

The results indicate that, under the controlled laboratory parameters used, BioGlide® grafted catheters demonstrated the ability to absorb and carry a quantity of antibiotic sufficient to inhibit bacterial growth for up to approximately 48 hours. The non-grafted control catheters, when similarly pre-soaked in antibiotic, exhibited no detectable inhibition of bacterial growth. It will be recognized that longer-term protection against infection may be desired, particularly when larger surgical wounds are created, e.g., implantation of a drug pump, neurostimulator, etc.

Medical Device

Various embodiments of the invention provide an implantable medical device 10 comprising a body member 12 into, onto, or about which an anti-infective agent 20 or an anti-activity agent 200 is disposed. The medical device 10 may be any implantable medical device, such as a lead, a catheter, a needle, a neurostimulator, a pacemaker, a defibrillator, a drug infusion pump, and the like. Anti-infective agent 20 or anti-activity agent 200 may be associated with the surface of the implantable medical device 10 in any fashion such that, after implanting the device 10, an infection may be prevented. For the sake of convenience, FIGS. 1-4 shown medical device 10 as a catheter comprising a lumen 15, but it should be understood that the discussion regarding these figures may be applicable to any implantable medical device 10, whether or not is comprises a lumen 15.

Figure 2:
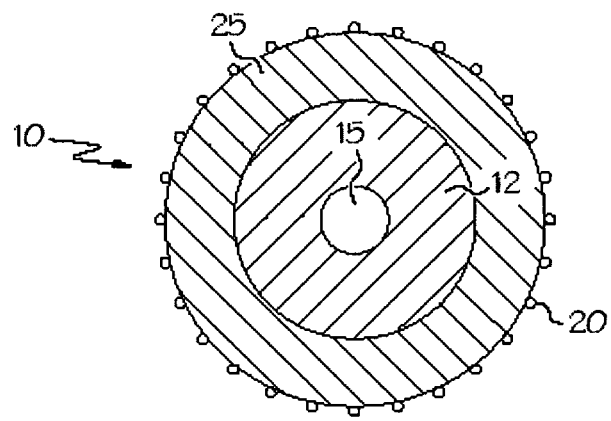
FIG. 2 is a diagrammatic illustration of a cross-section of a device comprising anti-infective agent disposed on the surface of a coating layer of the device.
Figure 3:
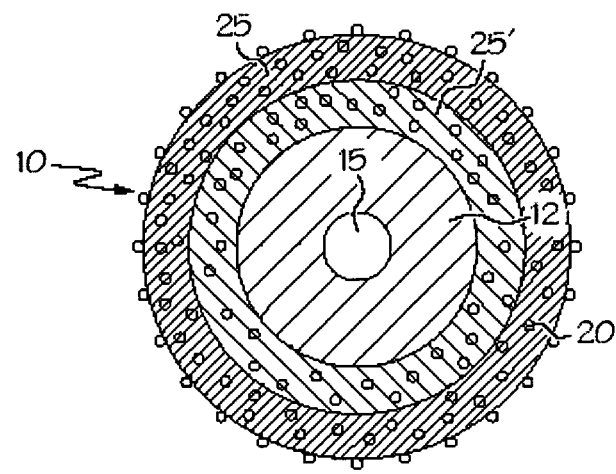
FIG. 3 is a diagrammatic illustration of a cross-section of a device comprising anti-infective agent disposed in an intermediate layer and an outer layer of the device.

FIGS. 1-3 show examples of associations of anti-infective agent 20 with surface of medical device 10. FIG. 1 shows that anti-infective agent 20 may be disposed in coating layer 25 disposed about a body member 12 of device 10. Coating layer 25 may be a vehicle, such as a polymeric vehicle. While FIG. 1 shows anti-infective agent 20 disposed throughout the coating layer 25, the anti-infective agent 20 may be disposed within one or more portions of the coating layer 25 (not shown). FIG. 2 shows that anti-infective agent 20 may be disposed on the surface of the coating layer 25. If a given anti-infective agent 20 is disposed partially within the coating layer 25 or body member 12 or other layer and partially protrudes from a surface of the coating layer 25 or body member 12 or other layer, the anti-infective agent 20 is considered both disposed in and disposed on the coating layer 25 or body member 12 or other layer. Further, while not shown, it will be understood that anti-infective agent 20 may be both disposed in and disposed on the coating layer 25, body member 12, or other layer of the delivery element 10.

It will be understood that anti-infective agent 20 as depicted in FIGS. 1 and 2, other subsequent Figures, and throughout the present disclosure may refer to a plurality of different anti-infective agents 20. For example, a given anti-infective agent 20 depicted in FIG. 1A may be, e.g., rifampin and a different anti-infective agent 20 may be, e.g., minocycline.

In various embodiments of the invention, anti-infective agents 20 are disposed on or in more than one layer of device 10. For example, anti-infective agent 20 may be disposed on or in a body member 12 of device 10 or on or in one or more coating layer 25 of device 10. FIG. 3 shows an embodiment where anti-infective agent 20 is disposed on or in a first coating layer 25 and on or in a second coating layer 25'. Of course, two, three, four, five, six, or more coating layers 25 may be disposed about body member 12 of device 10 and anti-infective agent 20 may be disposed in or on the body member 12 or none, some, or all of the one or more coating layers 25, 25'.

Figure 4:
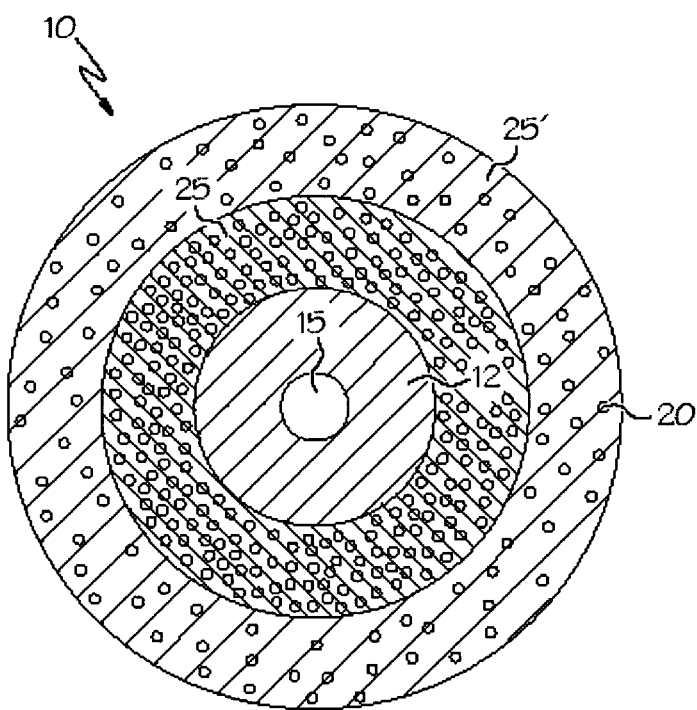
FIG. 4 is a diagrammatic illustration of a cross-section of a device comprising varying concentrations of anti-infective agent disposed in an intermediate layer and an outer layer of the device.

The concentration of anti-infective agent 20 within various layers (depicted as body member 12 or coating layer 25, 25') may be the same or different. Any concentration may be used. For example, anti-infective agent 20 may comprise about 0.1% to about 50%, or from about 1% to about 10%, of the weight of the layer. In some circumstances, it may be desirable to place a higher concentration of anti-infective agent 20 in one or more layers relative to other layers. For example, to obtain a substantially constant release rate of anti-infective agent 20 over time it may be desirable for an underlying layer 25 and less in an overlying layer 25'. FIG. 4 shows a device 10, where first coating layer 25 comprises a higher concentration of anti-infective agent 20 within or on intermediate coating layer 25 than in outer coating layer 25' or body member 12. Anti-infective agent 20 may elute out of outer coating layer 25' into body tissue. Increased initial concentration of anti-infective agent 20 in intermediate coating layer 25 may effectively replenish the supply of anti-infective agent 20 in outer coating layer 25' such that anti-infective agent 20 may continue to elute into tissue as substantially the same concentration over time. Of course other variations are possible. For example, it may be desirable to place a faster eluting agent 20 in an intermediate layer 25 and a slower eluting agent 20 in an outer layer 25' such that the faster and slower eluting agents 20 reach the tissue at substantially the same concentration over a period of time.

Figure 5:
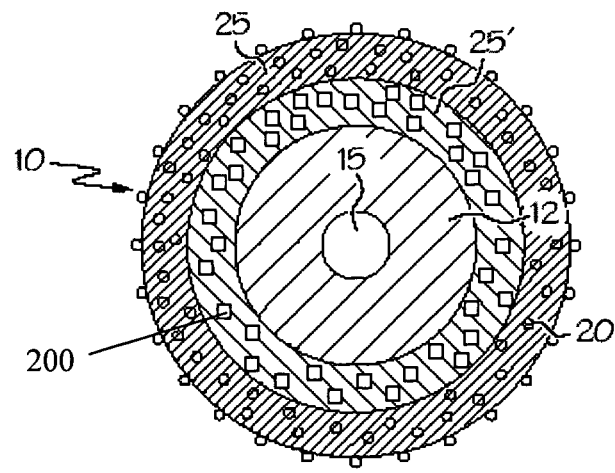
FIG. 5 is a diagrammatic illustration of a cross-section of a device comprising an anti-activity agent disposed in an intermediate layer and anti-infective agent disposed in an outer layer of the device.

In various embodiments of the invention, an anti-activity agent 200 is associated with device 10. If no anti-activity agent 200 is associated with device 10, it is preferred that coating layer 25, 25' be biodegradable and that the layer biodegrade as discussed for vehicle above. Referring to FIG. 5, anti-activity agent 200 is disposed in an intermediate layer 25 and anti-infective agent 20 is disposed in an outer layer 25' of device 10. Preferably, the intermediate layer 25 and outer layer 25' are configured to release the anti-activity agent 20 at therapeutic concentrations for a period (e.g., about 30 days, between about 30 days and about 90 days, or about 90 days) of time after implantation. This may be accomplished by loading appropriate amounts of anti-infective agent in one or more layers 25' of device. If layer 25' is biodegradable, the biodegradable nature of the vehicle may be controlled such that the layer 25' degrades at the appropriate time. The anti-infective agent 20 may elute from an intact layer 25' or may be released upon degradation of layer 25'. After a sufficient amount of time has passed (e.g., about 30 days, between about 30 days and about 90 days, or about 90 days) or after the concentration of anti-infective agent 20 becomes subtherapeutic, anti-activity agent 200 may be released from intermediate layer 25. Intermediate layer 25 may comprise biostable or biodegradable polymeric vehicle.

Figure 6:
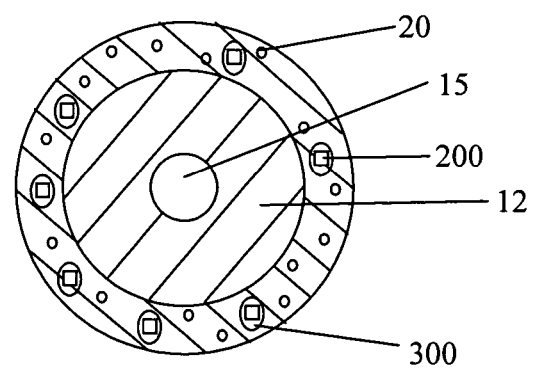
FIG. 6 is a diagrammatic illustration of a cross-section of a device comprising an anti-activity agent disposed in a vector disposed in a coating layer and anti-infective agent disposed in the coating layer of the device.

Of course, an anti-infective agent 20 and anti-activity agent may be present in the same layer 25 of device. To avoid premature interaction between the anti-activity agent 200 and the anti-infective agent 20, it may be desirable to incorporate either the anti-activity agent 200 or the anti-infective agent 20 into a vector 300. As shown in FIG. 6, the anti-activity agent 200 is incorporated into a vector, which is incorporated into the coating layer 25. The vector 300 may comprise a polymeric material different from a polymeric material of coating layer. The vector 300 may serve as a delayed release vehicle to release the anti-activity agent 200 at the appropriate time after implantation of the device 10.

Figure 7:
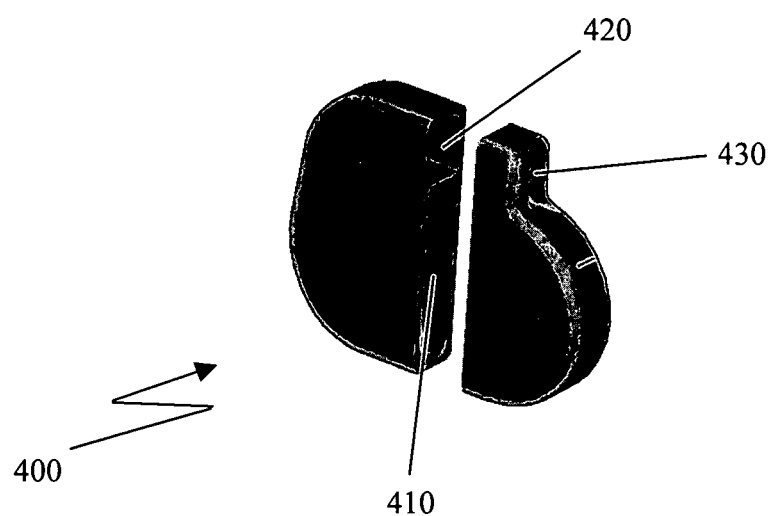
FIG. 7 is a diagrammatic illustration of a covering configured to receive an implantable medical device or portion thereof.

FIG. 7 shows an exemplary embodiment of a covering 400 configured to be disposed about an implantable medical device, such as a neurostimulator, a pacemaker, a drug infusion device, and the like. The covering may comprise one or more coating layers 25, 25' (not shown) into or onto which an anti-infective agent 20 or anti-activity agent 200 (not shown) may be disposed. The covering 400 depicted in FIG. 7 comprises an opening 410 configured to snuggly receive an implantable medical device. The covering 400 may also comprise an opening 420 for a header of the device and an opening 430 for an accessory device, such as a lead, a lead extension, or a catheter. It will be understood that covering may be in any form and may be adapted to be disposed about any implantable medical device. For example, covering may be a boot, a jacket, a sleeve, a sheath, and the like.

Coating layers 25, 25' may comprise polymeric materials designed to control the rate at which anti-infective agent 20 or anti-activity agent 200 is released, leached, or diffused from the polymeric material. As used herein, "release", "leach", "diffuse", "elute" and the like are used interchangeably when referring to a anti-infective agent 20 or anti-activity agent 200 with respect to a vehicle, coating layer 25 or body member 12 of a delivery element. Any known or developed technology may be used to control the release rate. For example, a coating layer may be designed according to the teachings of WO/04026361, entitled "Controllable Drug Releasing Gradient Coating for Medical Devices."

Coating layer 25 of delivery element 10 may be in the form of a tube, sheath, sleeve, coating, or the like. Coating layer 25 may be extruded, molded, coated on body member 12, grafted onto body member 12, embedded within body member 12, adsorbed to body member 12, etc. Polymers of coating layers 25 may be porous or non-porous. Porous materials known in the art include those disclosed in U.S. Pat. No. 5,609,629 (Fearnot et al.) and U.S. Pat. No. 5,591,227 (Dinh et al.). Typically polymers are non-porous. However, non-porous polymers may be made porous through known or developed techniques, such as extruding with $CO_2$ or by foaming the polymeric material prior to extrusion or coating.

Depending upon the type of materials used to form coating layers 25, the coatings can be applied to the surface of a body member 12 or underlying coating layer 25 through any coating processes known or developed in the art. One method includes directly bonding the coating material to a surface of body member 12 or underlying coating layer 25. By directly attaching a polymer coating to the body member 12 or underlying coating layer 25, covalent chemical bonding techniques may be utilized. Body member 12 or underlying coating layer 25 surface may possess chemical functional groups on its surface such as carbonyl groups, primary amines, hydroxyl groups, or silane groups which will form strong, chemical bonds with similar groups on polymeric coating material utilized. In the absence of such chemical forming functional group, known techniques may be utilized to activate the material's surface before coupling the biological compound. Surface activation is a process of generating, or producing, reactive chemical functional groups using chemical or physical techniques such as, but not limited to, ionization, heating, photochemical activation, oxidizing acids, sintering, physical vapor deposition, chemical vapor deposition, and etching with strong organic solvents. Alternatively, the coating layer 25 may be indirectly bound to body member 12 or underlying coating layer 25 through intermolecular attractions such as ionic or Van der Waals forces.

Anti-infective agent 20 or anti-activity agent 20 may be incorporated into a coating layer 25 in a variety of ways. For example, anti-infective agent 20 or anti-activity agent 20 can be covalently grafted to a polymer of the coating layer 25, either alone or with a surface graft polymer. Alternatively, anti-infective agent 20 or anti-activity agent 20 may be coated onto the surface of the polymer either alone or intermixed with an overcoating polymer. Anti-infective agent 20 or anti-activity agent 20 may be physically blended with a polymer of a coating layer 25 as in a solid-solid solution. Anti-infective agent 20 or anti-activity agent 20 may be impregnated into a polymer by swelling the polymer in a solution of the appropriate solvent. Any means of incorporating anti-infective agent 20 or anti-activity agent 20 into or on a coating layer 25 may be used, provided that anti-infective agent 20 or anti-activity agent 20 may be released, leached or diffuse from coating layer 25 on or after contact of device 10 with bodily fluid or tissue.

A polymer of a coating layer 25 and an anti-infective agent 20 or anti-activity agent 20 may be intimately mixed either by blending or using a solvent in which they are both soluble. This mixture can then be formed into the desired shape or coated onto an underlying structure of the medical device. One exemplary method includes adding one or more anti-infective agent 20 or anti-activity agent 20 to a solvated polymer to form a anti-infective agent 20/polymer solution or anti-activity agent 200/polymer solution or anti-infective agent 20/anti-activity agent 200/polymer solution. The agent/polymer solution can then be applied directly to the surface of body member 12 or underlying coating layer 25; for example, by either spraying or dip coating device 10. As the solvent dries or evaporates, the agent/polymer coating is deposited on body member 12. Furthermore, multiple applications can be used to ensure that the coating is generally uniform and a sufficient amount of agent has been applied to device 10.

Alternatively, an overcoating polymer, which may or may not be the same polymer that forms the primary polymer of body member 12 or underling coating layer 25, and anti-infective agent 20 or anti-activity agent 20 are intimately mixed, either by blending or using a solvent in which they are both soluble, and coated onto body member 12 or underling coating layer 25. Any overcoating polymer may be used, as long as the polymer is able to bond (either chemically or physically) to the polymer of an underlying layer of delivery element 10.

In addition, a polymer of a coating layer 25 may be swelled with an appropriate solvent, allowing an anti-infective agent 20 or anti-activity agent 20 to impregnate the polymer.

Anti-infective agent 20 or anti-activity agent 20 may also be covalently grafted onto a polymer of a coating layer 25. This can be done with or without a surface graft polymer. Surface grafting can be initiated by corona discharge, UV irradiation, and ionizing radiation. Alternatively, the ceric ion method, previously disclosed in U.S. Pat. No. 5,229,172 (Cahalan et al.), may be used to initiate surface grafting.

All printed publications, such as patents, patent applications, technical papers, and brochures, cited herein are hereby incorporated by reference herein, each in its respective entirety. As those of ordinary skill in the art will readily appreciate upon reading the description herein, at least some of the devices and methods disclosed in the patents and publications cited herein may be modified advantageously in accordance with the teachings of the present invention.

What is claimed is:

1. An implantable medical device comprising:
    a structural body member having a surface;
    an anti-infective agent having anti-infective activity disposed on or in a first vehicle, the first vehicle being disposed on, or about at least a portion of the surface of the structural body member; and
    an anti-activity agent is disposed in a second vehicle, the second vehicle being disposed on, in, or about at least a portion of the surface of the structural body member, the anti-activity agent selected to interfere with anti-infective activity of the anti-infective agent,
    wherein the anti-activity agent is citric acid and the anti-infective agent is rifampin,
    wherein the device is configured to delay release of the anti-activity agent from the surface of the body member until between about thirty days and about 90 days after the device is implanted in a subject.

2. The device of claim 1, wherein the first vehicle is biodegradable.

3. The device of claim 2, wherein the first vehicle is configured to degrade within thirty days of the device being implanted in a tissue location of a subject.

4. The device of claim 2, wherein the first vehicle is configured to degrade within between thirty days and ninety days of the device being implanted in a tissue location of a subject.

5. The device of claim 2, wherein the first vehicle is configured to degrade within about ninety days of the device being implanted in a tissue location of a subject.

6. The device of claim 1, wherein the second vehicle disposed on or about at least a portion of the surface of the body member and the first vehicle is disposed on or about at least a portion of the second vehicle.

7. The device of claim 6, wherein the first vehicle is biodegradable.

8. The device of claim 1, wherein the first vehicle forms a layer disposed on or about at least a portion of the surface of the body member and the second vehicle is disposed within the layer.

9. The device of claim 1, wherein the anti-infective agent and the anti-activity agent are disposed in a covering disposed about at least a portion of the surface of the body member.

10. The device of claim 1, wherein the anti-activity agent is configured to be released from the surface of the body member about thirty days after the device is implanted in a subject.

11. The device of claim 1, wherein the anti-activity agent is configured to be released from the surface of the body member between about thirty days and about 90 days after the device is implanted in a subject.

* * * * *